(12) United States Patent
Levisman

(10) Patent No.: US 7,479,010 B2
(45) Date of Patent: Jan. 20, 2009

(54) THREADED IMPLANT WITH IMPROVED DISTAL END

(76) Inventor: Ricardo Levisman, Agüero 1292 1 st Floor, 1425 Buenos Aires (AR)

( * ) Notice: Subject to any disclaimer, the term of this patent is extended or adjusted under 35 U.S.C. 154(b) by 19 days.

(21) Appl. No.: 11/327,882

(22) Filed: Jan. 9, 2006

(65) Prior Publication Data

US 2007/0160956 A1    Jul. 12, 2007

(51) Int. Cl.
*A61C 8/00*    (2006.01)
(52) U.S. Cl. ................................................. 433/174
(58) Field of Classification Search .......... 433/172–176
See application file for complete search history.

(56) References Cited

U.S. PATENT DOCUMENTS

| | | | |
|---|---|---|---|
| 3,579,831 A * | 5/1971 | Stevens et al. | 433/174 |
| 4,407,620 A | 10/1983 | Shinjo | |
| 4,915,560 A * | 4/1990 | Peterson et al. | 411/378 |
| 4,963,064 A * | 10/1990 | Peterson | 411/387.5 |
| 5,064,327 A * | 11/1991 | Hughes | 411/386 |
| 5,897,319 A | 4/1999 | Wagner et al. | |
| 6,315,564 B1 | 11/2001 | Levisman | |
| 6,334,747 B1 * | 1/2002 | Torisu et al. | 411/386 |
| 6,350,126 B1 | 2/2002 | Levisman | |
| 6,382,976 B1 | 5/2002 | Wagner | |
| 6,468,013 B1 * | 10/2002 | Kersten | 411/386 |
| 6,506,051 B2 | 1/2003 | Levisman | |
| 2003/0165796 A1 * | 9/2003 | Carmichael et al. | 433/174 |
| 2004/0072128 A1 | 4/2004 | Klardie et al. | |
| 2005/0019731 A1 | 1/2005 | Bjorn et al. | |
| 2005/0065525 A1 * | 3/2005 | Aringskog et al. | 606/72 |
| 2005/0147943 A1 | 7/2005 | Chang | |
| 2005/0250074 A1 * | 11/2005 | Lang et al. | 433/174 |
| 2006/0127849 A1 | 6/2006 | Levisman | |

FOREIGN PATENT DOCUMENTS

WO    WO 03/020154 A1 *    3/2003

* cited by examiner

*Primary Examiner*—Ralph A Lewis
(74) *Attorney, Agent, or Firm*—Greer, Burns & Crain, Ltd.

(57) ABSTRACT

A dental implant with improved cuffing distal end for preventing the implant from stagnating along a bone socket during implantation includes an implant body having a head for receiving a dental prosthesis and a root for anchoring into a bone of a patient; wherein the root is truncated at a distal portion thereof to form an inclined sharp cutting face.

9 Claims, 3 Drawing Sheets

THREADED IMPLANT WITH IMPROVED DISTAL END

BACKGROUND OF THE INVENTION

1. Field of the Invention

The present invention relates to implants and prosthesis generally employed in the medical field for repairing or recovering body pieces such as bone pieces, dental pieces, and the like, and more particularly the invention refers to a dental implant, preferably a threaded dental implant, provided with enhanced and improved cutting means at a root of the implant, preferably at a distal end of the implant.

While the present specification makes reference to dental implants as preferred embodiments of the invention it must be clear that the teachings of the invention may be applied to any implant or prosthesis that is to be installed into a bone.

2. Description of the Prior Art

Prosthesis and implants are well known in the medical field; they are employed in connecting broken bones and replacing lost body pieces. More precisely, in the odontology field, dental implants are being more and more employed to replace lost dental pieces, with the implants comprising basically an implant body that is fixed into the maxillary bone by screwing-in or nailing the implant into a bone hole such as the drilled bore or recent post extraction socket in the bone of a patient. Several techniques may be employed to permit correct osseous integration of the implant body into the bone and to wait for healing of the bone and gum. After the healing and integration period an abutment may be fixed into the implant body and a dental prosthesis or crown may be finally mounted and fixed, by screws or cement, onto the abutment and implant body. In some implantation techniques no healing period is waited for and the dental prosthesis and abutment are mounted and fixed to the implant body immediately after the same has been inserted and fixed into the bone.

In any of the techniques presently in practice always the implant must be firmly anchored into the bone in order to prevent undesired movements thereof during healing or after healing. Another problem or difficulty is that when the implant must be installed into the bone bore the length of the implant must be in agreement to the depth of the bore or socket. Preferably, the implant should have exactly the same depth of the bore in order to be firmly retained and anchored against the bottom of the bore. However, this is not an easy task. While the implantologist may take exact measures of the bore depth and the implant length in order to have the bore drilled with the appropriate depth, the irregularities of the bore walls and bottom cause the implant to be usually stagnated into the bore before reaching the bottom as recommended or it contacts the bottom of the bore before reaching the necessary implant-bone interference to be anchored against the bore walls.

If the implant is screwed into the bone and it results stagnated or -firmly anchored against the lateral walls of the bore without reaching and contacting the bottom of the bore, the implant would result in an improper installation with the future disassembling consequences. However, while the implantologist or dentist becomes aware of the misfit and deficient installation generally he/she are not able to remove the implant as long as it has already been firmly wedged into the bore and, if stronger forces are applied onto the implant to remove it from the bore it is quite frequent that the implant body is broken with a part thereof remaining into the bore and with the drastic consequences this may imply.

The reasons of the above difficulties are, among others, the matching complex shapes and materials involved in the attachment as well as the plasticity of the jawbone which is capable of capturing the metallic implant into a firm stagnated position before reaching the bottom of the socket. These difficulties increase as long as the outer surfaces of the implants are provided with means for enhancing osseous integration such as outer surface textures, pores, etc. which causes a problem in the displacement of the implant. When the smooth rounded end of the implant body does not contact the bottom of the socket the threads at the upper or proximal portion of the body do not get enough anchoring against the socket walls. This also prevents the desired helical implant advance, some times, at the beginning of the insertion process.

While an oversized hole depth of about 2 mm serves to more easily position a tapered implant at the correct proximal level this can not be carried out when the patient has a reduced bone height. In addition, a tapered screw can be inserted more easily into a cylindrical drilled bone bore but in detriment of a strong initial stability.

There are a variety of implant systems employing enhanced cutting means at the distal ends thereof to help cutting the bore walls while the implant is being screwed into the bone. An implant of this type is disclosed in U.S. Patent Application published under No. U.S. 2005/0019731 A1 to Bjorn et al. wherein the implant is a self-tapping one including one or more bone-chip recesses for accommodating bone material cut-off during the tapping operation. While the cutting edges defined by the recesses and the threads operate well to cut off the bone, the bottom of the implant is blunt and flat enough to abut against the bottom of the bone socket in a manner to prevent the implant from entering deeper into the socket as long as the cutting off action is exerted only against the vertical walls of the socket.

Other implants having similar cutting recesses are disclosed in published U.S. 2005/0147943 A1; U.S. 2004/0072128 A1; U.S. Pat. No. 5,897,319 and U.S. Pat. No. 6,382,976 B1, all having blunt bottoms or ends that prevent the correct deep cutting off to enter the bone mass. While other implants like the one of U.S. Pat. No. 4,407,620 are provided with sharper ends and cutting edges, the entire implant body rotates in the central point of the bottom tip without permitting to carry out an effective cutting effect and, as an opposite effect, the tip is frequently wedged into the bone mass of the socket bottom preventing the cutting edges from properly cutting off the socket vertical walls. In other words, the central bottom tip operates as a pivot point barring any cutting capacity of the implant.

While the use of cutting grooves for dental implants has been widely extended there are circumstances where the use thereof leads to inconvenient results. As a result of the drilling or cutting action of the grooves the sticky bone material collected into the grooves may cause the implant to be prematurely stacked into the socket. For solving this question the grooves have been made to extend all along the entire length of the implant body with the risk that the body may fracture due to the diminished resistant section of the implant.

According to a well known theory, the hydraulic pressure exerted within the isolated distal space, without immediate drainage, indirectly affects the desired results. To permit the escape of hydraulic pressure, caused by the blood and the grafting material, during the insertion procedure, two or more parallel grooves have been provided. Differing from the well known shorter cutting grooves, these larger grooves extend all along the length of the implant body.

The inventor has found that all of the above improvements in dental implants, while working acceptably, had not provided a final and integral solution to the above disclosed problems of mismatching and lack of firm installation of the implant body into the bone socket.

It would be therefore convenient to have an implant with improved cutting and pressure relief means at the root or distal end of the implant to guarantee a firm and proper installation of the implant into the bone socket.

SUMMARY OF THE INVENTION

It is therefore an object of the invention to provide a dental implant having a dental body with a root for anchoring into a bone of a patient, the root including a cutting face extending across the entire root along a diagonal pattern to form a cavity between the root and bone when implanted.

It is still another object of the present invention to provide a dental implant with improved cutting distal end comprising an implant body having a head for receiving a dental prosthesis and a root for anchoring into a bone of a patient, wherein the root is diagonally truncated at a distal portion thereof to form an inclined cutting face.

It is a further object of the present invention to provide a dental implant with improved cutting distal end comprising an implant body having a head for receiving a dental prosthesis and a root for anchoring into a bone of a patient, wherein the root is diagonally truncated at a distal portion thereof to form an inclined sharp cutting face extending diagonally across the root and asymmetrically relative to a longitudinal geometrical axis of the implant, whereby the cutting face extends from a distal end of the root at one larger side thereof to an opposite shorter side of the root.

It is a further object of the present invention to provide a dental implant with improved cutting distal end comprising an implant body having a head for receiving a dental prosthesis and a root for anchoring into a bone of a patient, wherein the root is truncated at a distal portion thereof to form an inclined sharp cutting face including a bottom cutting groove at a bottom portion of the cutting face.

It is still a further object of the present invention to provide a dental implant with improved cutting distal end comprising an implant body having a head for receiving a dental prosthesis and a root for anchoring into a bone of a patient, wherein the root is truncated at a distal portion thereof to form an inclined cutting face including an upper cutting groove at an upper portion of the cutting face.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
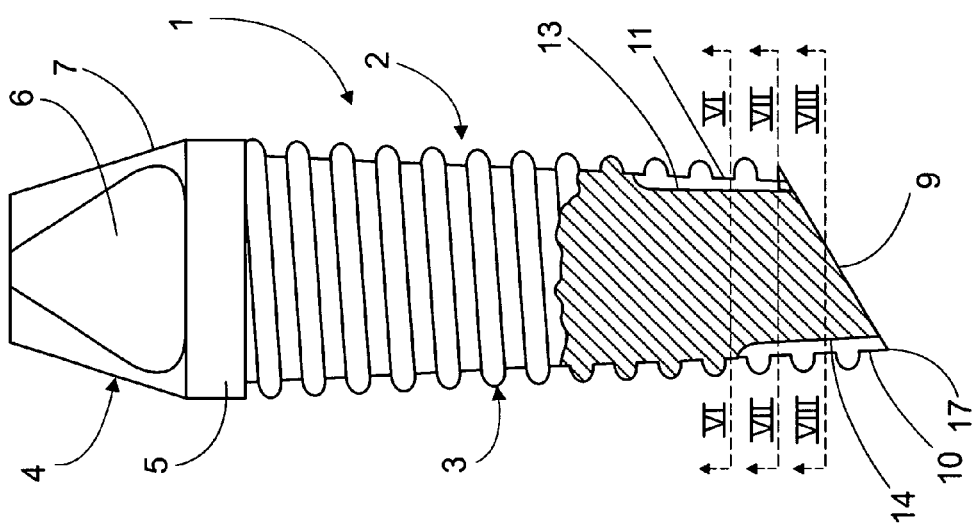
FIG. 1 shows an elevational side view of dental implant body according to the present invention.

Now referring in detail to the invention, the dental implant according to the invention comprises an implant body 1 with a root portion 2 generally of a conical or tapered shape including a plurality of threads 3 and a head portion or head 4, preferably having a frustoconical profile as disclosed in U.S. Ser. No. 11/012,931 to the same inventor of the present application and the contents of which are included as a reference in the present application. The implant body with its corresponding portions is made preferably of a bio-compatible material, such as a metal, more preferably titanium and most preferably titanium that is chemically treated, for example by an osseous conductive substance, to have an outer surface for promoting the osseous integration of the implant into the patient's bone. Root portion 2 and head portion 4 are preferably separated by a collar portion 5, preferably a cylindrical body portion, free of threads. Threads 3 may be of any convenient and/or desired design but, preferably, they are of a retentive type, such as of a rounded profile, as disclosed in U.S. Pat. No. 6,315,564 to the same inventor as the present application and the contents of which are included as a reference in this application.

Figure 4:
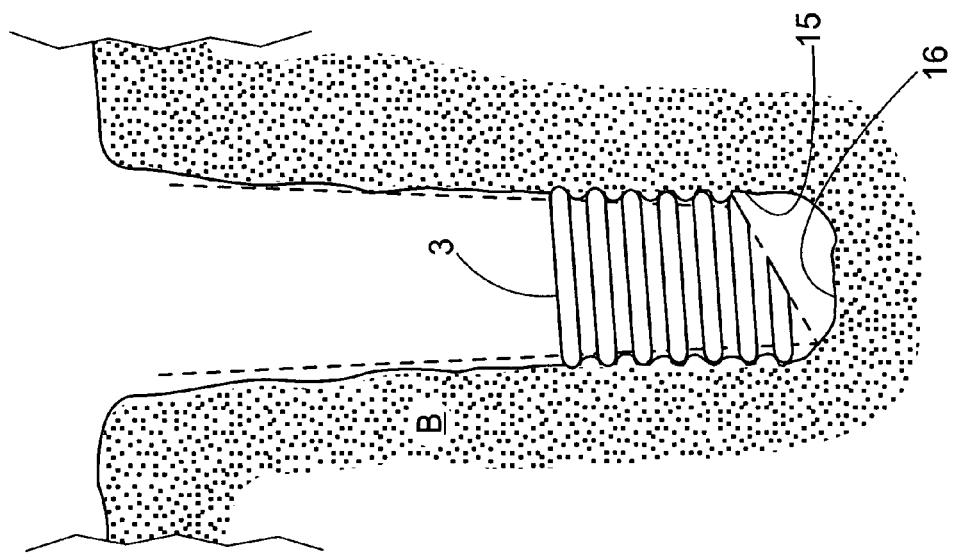
FIGS. 4 and 5 are side elevational views showing how the implant enters a bone socket and the threads enter the bone mass.
Figure 5:
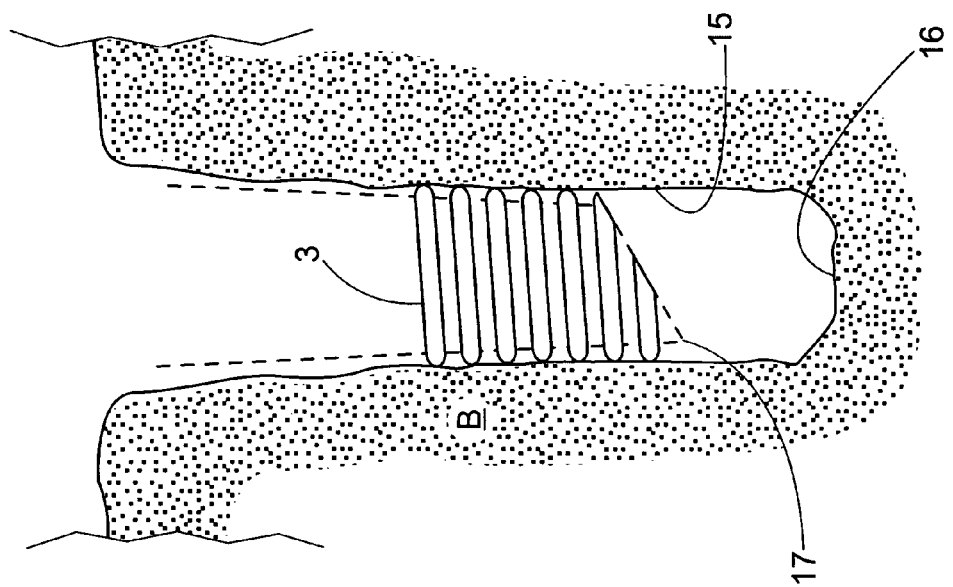
Figure 8:
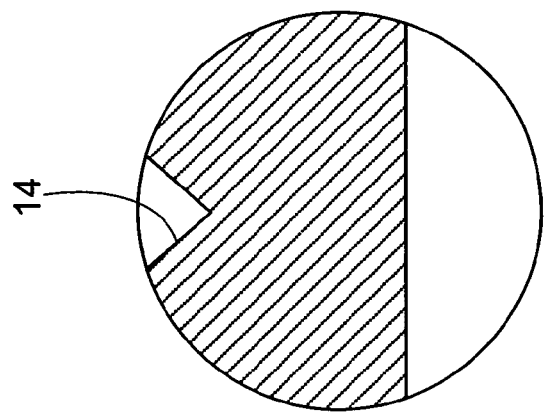
FIGS. 6-8 show respective cross-sectional views of the distal end of the implant taken along lines VI-VI; VII-VII and VIII-VIII of FIG. 3.
Figure 7:
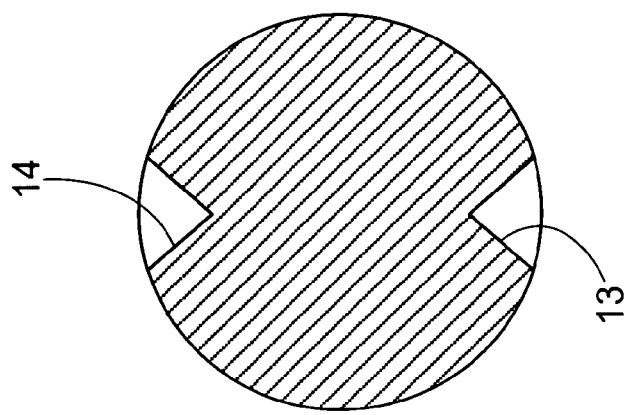
Figure 6:
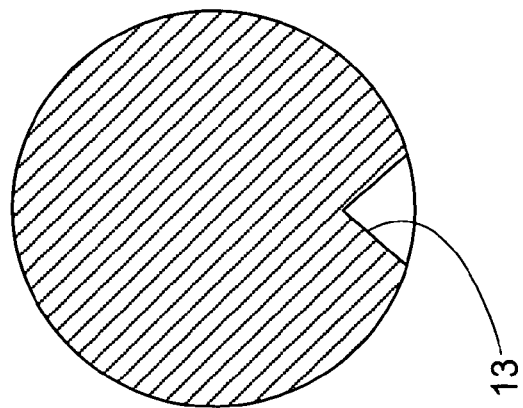

Head portion 4 has an anti-rotational design, preferably a nut-shaped outer contour comprised of several faces 6 for fit-receiving a wrench, not shown, or any other tool as it is well known in the art, for installing the implant into a bone "B" of a patient, FIGS. 4-6. Head 4 may be provided with any other type of screwing means for installing the implant into the bone as well as it may include a bore or any mounting means for receiving an abutment and a prosthesis as it is well known in the art. Any abutment and/or prosthesis will be fixed onto a frustoconical surface 7 by means of a proper cement, mechanical interference, etc. as it is well known in the art.

According to the invention, the dental implant is provided with improved cutting means at the distal end thereof. More particularly, root 2 is truncated at distal end or portion 8 to form an inclined cutting face 9. More precisely, cutting face 9 extends diagonally and entirely across the root, from a distal end of the root at one larger side 10 of the root to an opposite shorter side 11 of the root.

Figure 2:
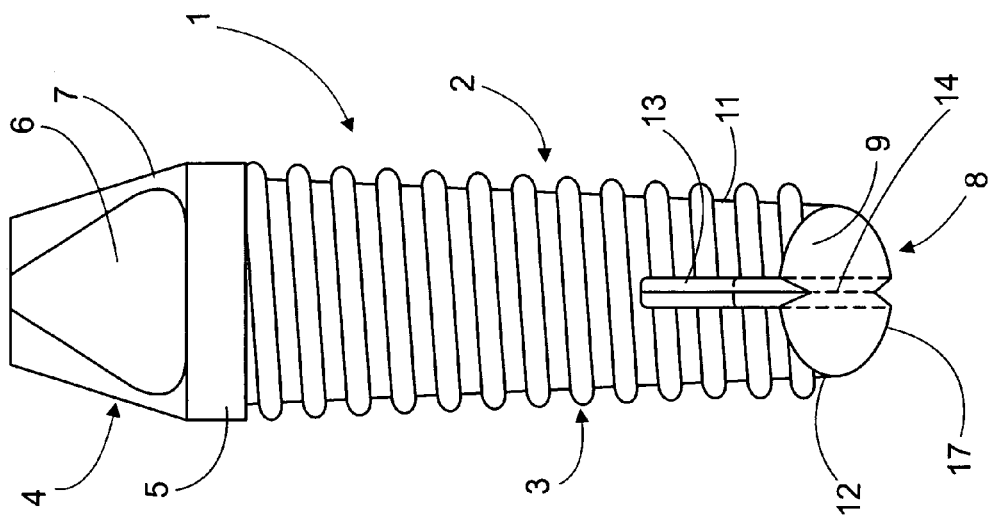
FIG. 2 shows an elevational front view of the implant body of FIG. 1.
Figure 3:
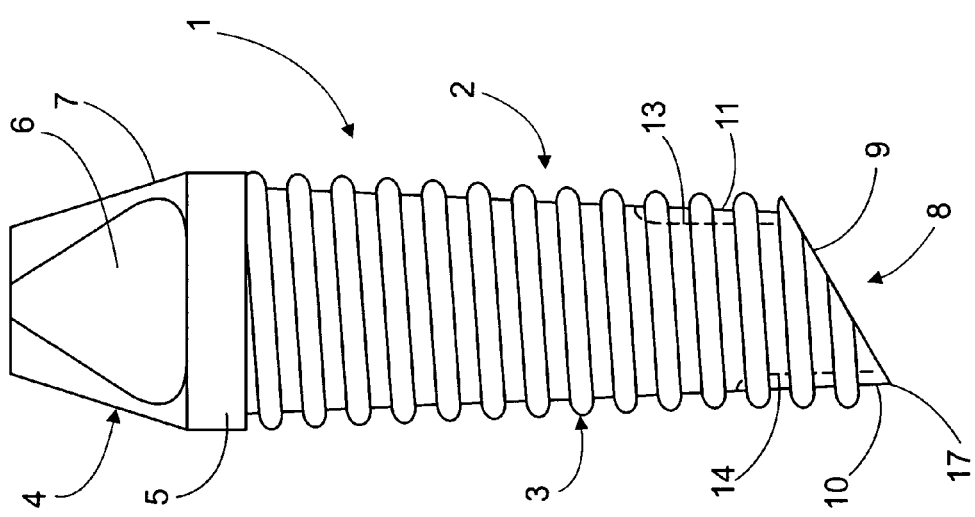
FIG. 3 shows an elevational side view of the implant body of FIG. 1 in partial cross-section.

Depending on the inclination of cutting face 9, this face may have a circular or oval configuration as shown in FIG. 2. In addition, cutting face 9 may be entirely or partially planar or concave and may define peripheral sharp cutting edges 12. While cutting face 9 may have a variety of configurations and extension but preferably it extends along a length comprising from about the 5% to about the 30% of the entire length of the implant body.

While the provision of cutting face 9 has demonstrated a satisfactory cutting action it may be enhanced by the provision of at least one additional cutting groove, namely an upper groove 13 and/or a bottom groove 14. In effect, cutting face 9 may include upper cutting groove 13 at an upper portion of the cutting face. More particularly, upper cutting groove 13 is a V-shaped groove and extends partially along shorter side 11 of the root, outside cutting face 9, and partially along the cutting face.

In addition, cutting face 9 also or alternatively may include bottom cutting groove 14 at a bottom portion of the cutting face. More particularly, bottom cutting groove 14 is a V-shaped grooved and extends partially along larger side 10 of the root, outside cutting face 9, and partially along the cutting face.

In order to install the inventive implant in a patient, the implant body 1 is taken, for example by means of a clip, and inserted into a bore or socket 15 of a bone "B". Bore 15 may be a drilled bore or a recent post-extraction socket. Once the implant body is inserted into bone "B", a tool or wrench, not illustrated, is coupled to head 4 and it is operated by rotation to screw implant body 1 into bone socket 15. Threads 3, such as the ones of inventor's U.S. Pat. No. 6,315,564, will exert a pressure against the bone enough to provide a strong retention of body 2 into bore 15 and to promote the bone growth around the implant body and the threads.

If the distal end of the implant would be, as it is known from the prior art, of the blunt type, it would stop against bottom 16 of socket 15 and while the threads 3 are with capacity to cut off the bone form the socket walls, the cutting off would be insufficient to permit implant 1 to go deeply into socket 15. According to the teachings of the invention, implant 1 is provided with inclined cutting face 9 that defines a bottom cutting edge that moves circularly in the bottom of the socket with capacity to cut off the bone to permit implant 1 to enter deeply into the socket. It is demonstrated that it will be easier to bottom cutting edge 17 to cut off the bone walls as compared to other cutting edges provided at the side walls of root 2 or with cutting tips similar to those ones of conventional screws. One of the reasons is that bottom cutting edge 17 moves around the bottom of socket 15 without staying and/or pivoting in the same place or same point.

Also according to the invention and differing from the prior art, the fact that cutting face 9 is inclined across root 2 forming a larger side 10 and a shorter side 11, makes the distal end of root 2 more flexible than the one of a conventional implant. This is important at the time of reaching the bottom 16 because, when a typical implant having an entire root or end reaches the bottom of socket 15 it is wedged or stagnated against the socket walls. Differing from this, the truncated end of the invention permit the larger side 10 to have a resilient behaviour and, therefore, it may yield against the socket wall pressure and move towards the center line of the socket thus permitting the implant to move further into the socket. This effect, together to the one referring to the enhanced cutting off capacity of bottom cutting edge 17 allows implant 1 to enter more deeply into the socket as compared to the implants of the prior art.

While preferred embodiments of the present invention have been illustrated and described, it will be obvious to those skilled in the art that various changes and modifications may be made therein without departing from the scope of the invention as defined in the appended claims.

I claim:

1. A dental implant with improved cutting distal end for preventing the implant from stagnating along a bone socket during implantation, the implant comprising:
    an elongated implant body having a head at an upper proximal end of the implant body for receiving a dental prosthesis and a root extending distally below the head for anchoring into a bone of a patient;
    an inclined sharp cutting face in a truncated distal portion of the root, with the inclined sharp cutting face extending diagonally across the root, from a distal end of the root at one longer side of the root to an opposite shorter side of the root;
    an upper cutting groove extending partially along the shorter side of the root, outside the cutting face, and partially in the cutting face, and
    a bottom cutting groove extending partially along the longer side of the root, outside the cutting face, and partially in the cutting face, with the bottom cutting groove extending at a level below the upper cutting groove.

2. The implant of claim 1, wherein the cutting face has a general oval configuration.

3. The implant of claim 1, wherein the cutting face defines peripheral sharp cutting edges.

4. The implant of claim 3, wherein the cutting face is planar.

5. The implant of claim 3, wherein the cutting face is concave.

6. The implant of claim 1, wherein the cutting face longitudinally extends along a length comprising from about the 5% to about 30% of an entire length of the implant body.

7. The implant of claim 1, wherein the upper cutting groove is a V-shaped groove.

8. The implant of claim 1, wherein the bottom cutting groove is a V-shaped groove.

9. The implant of claim 1, wherein the root includes at least one retentive thread outside the cutting face.

* * * * *